US011243110B2

(12) United States Patent
Lin

(10) Patent No.: US 11,243,110 B2
(45) Date of Patent: *Feb. 8, 2022

(54) METHOD AND SYSTEM TO TRACK WEIGHT WITHOUT STEPPING ON A WEIGHT SCALE

(71) Applicant: Daniel Lin, San Francisco, CA (US)

(72) Inventor: Daniel Lin, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/667,907

(22) Filed: Oct. 30, 2019

(65) Prior Publication Data

US 2020/0064182 A1 Feb. 27, 2020

Related U.S. Application Data

(63) Continuation-in-part of application No. 16/150,245, filed on Oct. 2, 2018, now Pat. No. 10,466,094, which is a continuation-in-part of application No. 14/708,218, filed on May 9, 2015, now abandoned.

(60) Provisional application No. 61/991,327, filed on May 9, 2014.

(51) Int. Cl.

| G01G 19/44 | (2006.01) |
|---|---|
| G01G 19/52 | (2006.01) |
| G01G 23/36 | (2006.01) |
| A61B 5/00 | (2006.01) |
| A61B 5/0205 | (2006.01) |
| A61B 5/01 | (2006.01) |
| A61B 5/024 | (2006.01) |
| A61B 5/11 | (2006.01) |

(52) U.S. Cl.
CPC .......... *G01G 19/44* (2013.01); *A61B 5/0002* (2013.01); *A61B 5/6891* (2013.01); *A61B 5/6892* (2013.01); *A61B 5/746* (2013.01); *G01G 19/52* (2013.01); *G01G 23/36* (2013.01); *A61B 5/01* (2013.01); *A61B 5/024* (2013.01); *A61B 5/02055* (2013.01); *A61B 5/1118* (2013.01); *A61B 5/4812* (2013.01); *A61B 5/4866* (2013.01); *A61B 2560/0252* (2013.01)

(58) Field of Classification Search
CPC .. G01G 19/445; G01G 19/52; G01G 23/3742; G01G 23/18; G01G 23/3735
See application file for complete search history.

(56) References Cited

U.S. PATENT DOCUMENTS

| 5,269,388 | A | * | 12/1993 | Reichow | G01G 19/445 177/144 |
|---|---|---|---|---|---|
| 8,362,903 | B2 | * | 1/2013 | Lindh | G01G 19/44 340/573.1 |
| 8,475,367 | B1 | * | 7/2013 | Yuen | A61B 5/02007 600/300 |
| 2003/0111275 | A1 | * | 6/2003 | Sternberg | G01G 19/445 177/144 |
| 2004/0020694 | A1 | * | 2/2004 | Hall | A61G 7/0527 177/144 |

(Continued)

*Primary Examiner* — John Villecco

(57) ABSTRACT

Embodiments herein provide systems and methods tracking the weight of an individual situated on a furnishing such as a chair or bed. One method generally includes receiving weight data at a weight sensor that is situated to recognize a change in weight on the furnishing, confirming that a fitness device is proximately located to the weight sensor, and transmitting the received weight data to a hosted service.

19 Claims, 6 Drawing Sheets

(56) References Cited

U.S. PATENT DOCUMENTS

| | | | |
|---|---|---|---|
| 2004/0124017 A1* | 7/2004 | Jones | G01G 19/445 177/144 |
| 2006/0028350 A1* | 2/2006 | Bhai | G01G 19/445 340/666 |
| 2007/0180047 A1* | 8/2007 | Dong | G16H 40/67 709/217 |
| 2008/0097250 A1* | 4/2008 | Tochigi | A61B 5/6892 600/595 |
| 2008/0235872 A1* | 10/2008 | Newkirk | G06F 3/0481 5/600 |
| 2009/0278696 A1* | 11/2009 | Lindh | G01G 19/4146 340/573.1 |
| 2010/0225489 A1* | 9/2010 | Hinterlong | A61B 5/103 340/573.4 |
| 2010/0292598 A1* | 11/2010 | Roschk | A61B 5/4869 600/519 |
| 2010/0299840 A1* | 12/2010 | Brauers | A47C 31/123 5/658 |
| 2012/0053424 A1* | 3/2012 | Kenalty | G01L 19/0092 600/300 |
| 2012/0122430 A1* | 5/2012 | Hutchings | G01G 23/3742 455/414.1 |
| 2013/0074262 A1* | 3/2013 | Receveur | A61G 7/0527 5/600 |
| 2014/0039351 A1* | 2/2014 | Mix | A61B 5/6892 600/587 |
| 2014/0063180 A1* | 3/2014 | Sharma | G01G 23/3735 348/36 |
| 2014/0083779 A1* | 3/2014 | Sharma | G01G 19/44 177/1 |
| 2014/0142396 A1* | 5/2014 | Ricks | A61B 5/02055 600/301 |
| 2015/0101870 A1* | 4/2015 | Gough | C12Q 1/6841 177/211 |
| 2015/0107910 A1* | 4/2015 | Villard | G16H 20/60 177/25.12 |
| 2016/0033319 A1* | 2/2016 | Kovacs | A61B 5/0205 177/25.13 |
| 2016/0299001 A1* | 10/2016 | Petrucelli | A61B 5/0537 |
| 2017/0143282 A1* | 5/2017 | Kovacs | A61B 5/0022 |
| 2017/0146389 A1* | 5/2017 | Kovacs | G01G 19/50 |
| 2017/0148240 A1* | 5/2017 | Kovacs | H04L 63/0876 |
| 2018/0035918 A1* | 2/2018 | Emalfarb | G06K 9/00885 |
| 2019/0373854 A1* | 12/2019 | Satoh | A01K 1/0107 |
| 2020/0064182 A1* | 2/2020 | Lin | A61B 5/6894 |
| 2020/0107753 A1* | 4/2020 | Young | G06N 20/00 |
| 2020/0109985 A1* | 4/2020 | Young | A61B 5/0205 |

* cited by examiner

METHOD AND SYSTEM TO TRACK WEIGHT WITHOUT STEPPING ON A WEIGHT SCALE

CROSS-REFERENCE TO RELATED APPLICATIONS

The present invention is a continuation-in-part of and claims the benefit of patent application Ser. No. 16/150,245, filed on Oct. 2, 2018 and entitled "Method and System to Track Weight Without Stepping on a Weight Scale," which is a continuation-in-part of and claims the benefit of patent application Ser. No. 14/708,218, filed on May 9, 2015 and entitled "Method and System to Track Weight Without Stepping on a Weight Scale," which claims the benefit of U.S. provisional patent application 61/991,327 filed May 9, 2014 and entitled "Method and System to Track Weight Without Stepping on a Weight Scale," the entirety of which are all hereby incorporated by reference.

BACKGROUND

Modern day body weight scales not only measure a user's weight but also his body mass index (BMI), body fat, water weight, hydration percentage, heart rate, bone mass, air quality and various other health-related measurements (e.g., all such measurements generally referred to as "weight data" herein). These scales also store such weight data and enable an individual to track and analyze historical measurements. For example, the scales may include Bluetooth and/or Wi-Fi connectivity that enable them to communicate weight data to a corresponding software application (e.g., developed by a the scale's manufacturer or a partner thereof) running on the individual's computer system or mobile device, or to a corresponding service hosted by a third party (e.g., such as the scale's manufacturer) and accessible through the Internet (e.g., through a web application accessed through a browser) that stores the weight data, provides analytics on the weight data (e.g., to provide historical trends information and/or health advice to the individual), and provides a rich user interface for the user to interact with his weight data to gauge his overall health.

Despite the sophistication of these weight scales, many users do not use a weight scale consistently. Users typically experience some phases where they are more health conscious and are more likely to track their weight using a weight scale and other phases where they are less focused on health and are less likely to use the weight scale. Unfortunately, it is during the phases when users are less health conscious (e.g., and therefore are not tracking weight data) that weight and other health related attributes (that may be measured or indicated by weight data) may deteriorate and that the tracking of weight data would have otherwise provided an indication of such deterioration and/or encouragement to improve health.

SUMMARY

Systems and methods for tracking the weight of an individual who may be situated on a furnishing such as an office chair or a bed are disclosed herein. By tracking the weight data for an individual while he is sitting on a chair (e.g., while working) or sleeping in bed, the individual does not need to consciously weigh himself every time he is interested in learning about his weight. Since the individual often goes to work each day (and sits in the chair) or sleeps in the same bed every night, his weight will be automatically measured without his conscious involvement.

In one embodiment, a weight sensor that is situated to recognize a change in weight on a furnishing (such as a bed or a chair) receives weight data, for example, as a result of the individual sitting or lying on the furnishing. The weight sensor confirms that a fitness device of the individual is proximately located to the weight sensor (e.g., by confirming a Bluetooth connection) and then the received weight data is transmitted to a hosted service that provides a user interface to track weight patterns of the individual. Confirmation by the fitness device that it is proximately located to the furnishing suggests a high probability that the individual is the person sitting or lying on the furnishing. Upon such confirmation, other health-related data from the fitness device may also be transmitted to the hosted service. Such other health-related data can then be used by the hosted server to further confirm whether the received weight data corresponds to the individual. For example, if the other health-related data suggests that the individual is walking, then the hosted service may conclude that the received weight data does not correspond to the individual.

In another embodiment, a system for tracking the weight of an individual who may be situated on the furnishing (e.g., chair, bed, etc.) comprises a weight data sensor for receiving weight data, wherein a form of the weight data sensor is designed to be situated to recognize change in weight on the furnishing and the weight data sensor is configured to measure and transmit weight data when the weight on furnishing differs from a default weight of the furnishing. The system also includes a fitness device of the individual for receiving other health-related data of the individual and a remote server configured to (i) receive weight data from the weight sensor, (ii) receive other health-related data of the individual from the fitness device, (iii) determine whether the received weight data is unrelated to the weight of the individual by comparing the received other health-related data to past measurements of the other health-related data that correspond to past weight measurements of the individual, (iv) disregard the received weight data if the received weight data is determined to be unrelated to the weight of the individual, and (v) present a user interface to the individual to track weight patterns of the individual based on the received weight data.

In this manner, when the individual is interested in understanding his weight patterns, he need only log into the hosted service to see his weight and does not need at that time to step on a weight scale, which may or may not be available at that time. Furthermore, the ability to silently track the individual's weight also enables the hosted service to provide alerts to the individual in the event of too much weight loss or gain during a phase where the individual may not be consciously weighing himself to track such loss or gain.

DETAILED DESCRIPTION

Figure 1A:
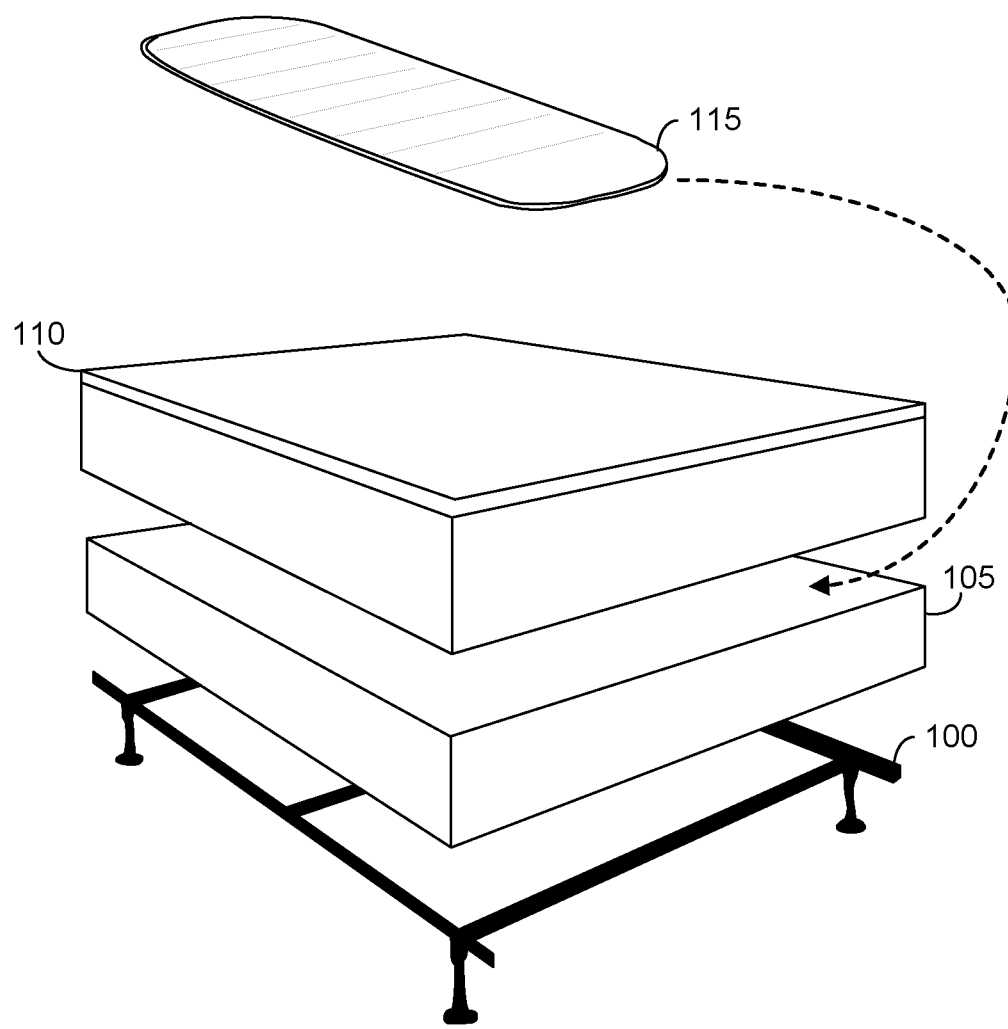
FIG. 1A depicts a weight data sensor that can be inserted underneath a mattress in accordance with one embodiment of the invention.

FIG. 1A depicts a weight data sensor that can be inserted underneath a mattress in accordance with one embodiment of the invention. A bed frame 100 supports a box spring 105 and a mattress 110. A weight data sensor 115 can be inserted underneath mattress 110, for example, between box spring 105 and mattress 110. As depicted in the embodiment of FIG. 1, weight data sensor 115 may take the form of an elongated pad that is long enough to experience an individual's full weight when the individual is lying on the bed, although it should be recognized that alternative form factors for weight data sensor 115 may be used consistent with the teachings herein. In addition to weight data, weight data sensor 115 may also be able to be able to monitor sleep patterns such as body movements, breathing cycles, heart rate, REM sleep patterns, deep sleep patterns, restless sleep patterns, etc.). Weight data sensor 115 may include Bluetooth, Wi-Fi or other radio wave or wireless communication capabilities that enable weight data sensor 115 to communicate with a local area network (LAN), a fitness device worn by an individual, a local computing device such as a smartphone, or with the Internet generally. In certain embodiments, weight data sensor 115 includes batteries or a power cord to plug into a nearby electric socket to provide power to drive the wireless communication capabilities and other digital functionality. Weight data sensor 115 also includes sensors to measure the weight (as well as other weight data in certain embodiments) of an individual when the individual is lying on mattress 110. For example, embodiments of a weight data sensor 115 may include a number of strain gauges (e.g., within a Wheatstone bridge, etc.) or other types of load cells (e.g., pneumatic, hydraulic, etc.) that measure compressive resistance change when an individual lies on mattress 110 and transmits a signal to a CPU or other circuit in weight data sensor 115 which convert the signal into a weight measurement. In certain embodiments, weight data sensor 115 may utilized air bladders to recognize change in pressure when an individual lies on the bed.

Figure 1B:
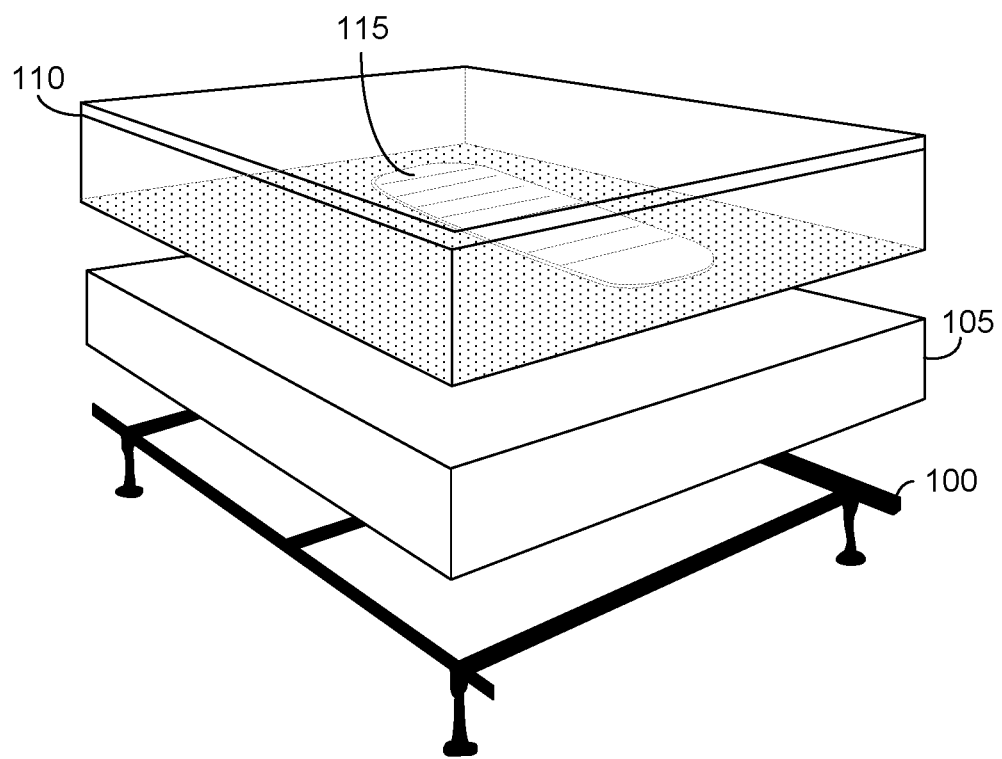
FIG. 1B depicts a weight data sensor that is embedded into a mattress in accordance with one embodiment of the invention.

FIG. 1B depicts an alternate embodiment of weight data sensor 115 that is embedded into mattress 110 in accordance with one embodiment of the invention. In one embodiment, mattress 110 may be an adjustable air mattress that utilizes air chambers and the load cells of weight data sensor 115 are incorporated as part of the air chamber mechanism such that the load cells experience compressive resistance change (e.g., to measure an individual's weight) in response to changes in the air pressure of the air chamber (as opposed to a separate elongated pad or similar insert as depicted in FIG. 1B). It should be recognized that FIGS. 1A and 1B are merely examples for a use case of the invention when the furnishing is a bed and/or mattress and that there are a number of ways to design the form factor as well as the weight-measuring mechanisms of weight data sensor 115 in order to accurately measure an individual's weight when the individual is situated on any type of furnishing such as an office chair, lounge chair, dining chair or sofa, as well as mattress 110. For example, rather than a single weight data sensor 115 created as a insertion pad like FIG. 1A or embedded into a mattress like FIG. 1B, other embodiments may use 4 separate weight sensors that may be placed under each of the four feet of a bed frame. As is known in the art, these 4 weight sensors can be designed to coordinate their measurements to determine a weight changed experienced by the bed.

Figure 2:
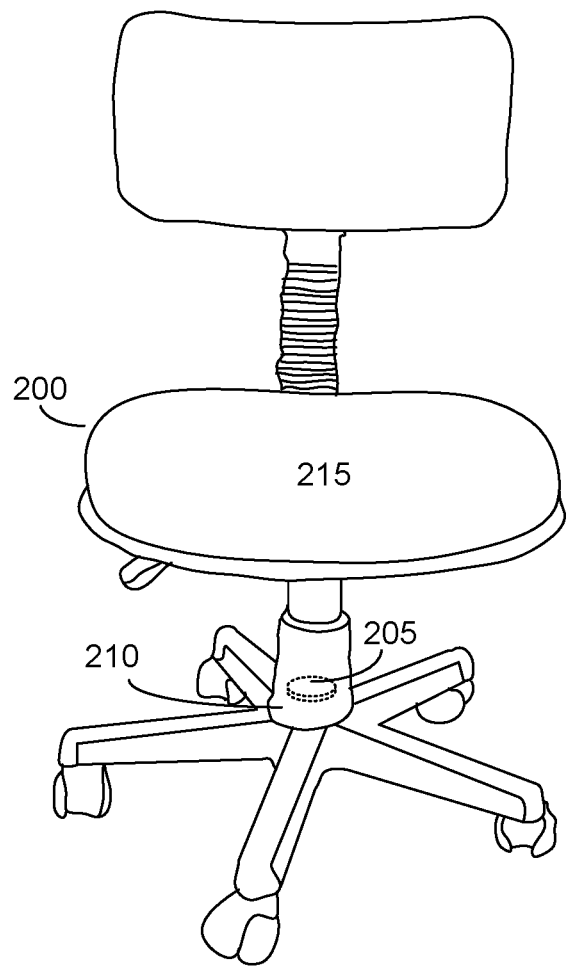
FIG. 2 depicts a weight data sensor that is situated in an office chair in accordance with one embodiment of the invention.

FIG. 2 depicts a weight data sensor 205 that is situated in an office chair 200 in accordance with one embodiment of the invention. Weight data sensor 205 is situated within the chair's cylinder 210 which bears the weight of the seat 215. Weight data sensor 205 can be functionality designed similarly to weight data sensor 115, for example, being configured with Bluetooth, Wi-Fi and/or other radio wave or wireless communication capabilities to communicate wirelessly with an individual's fitness device or smartphone or even to communicate with a hosted service as discussed further herein.

Figure 3:
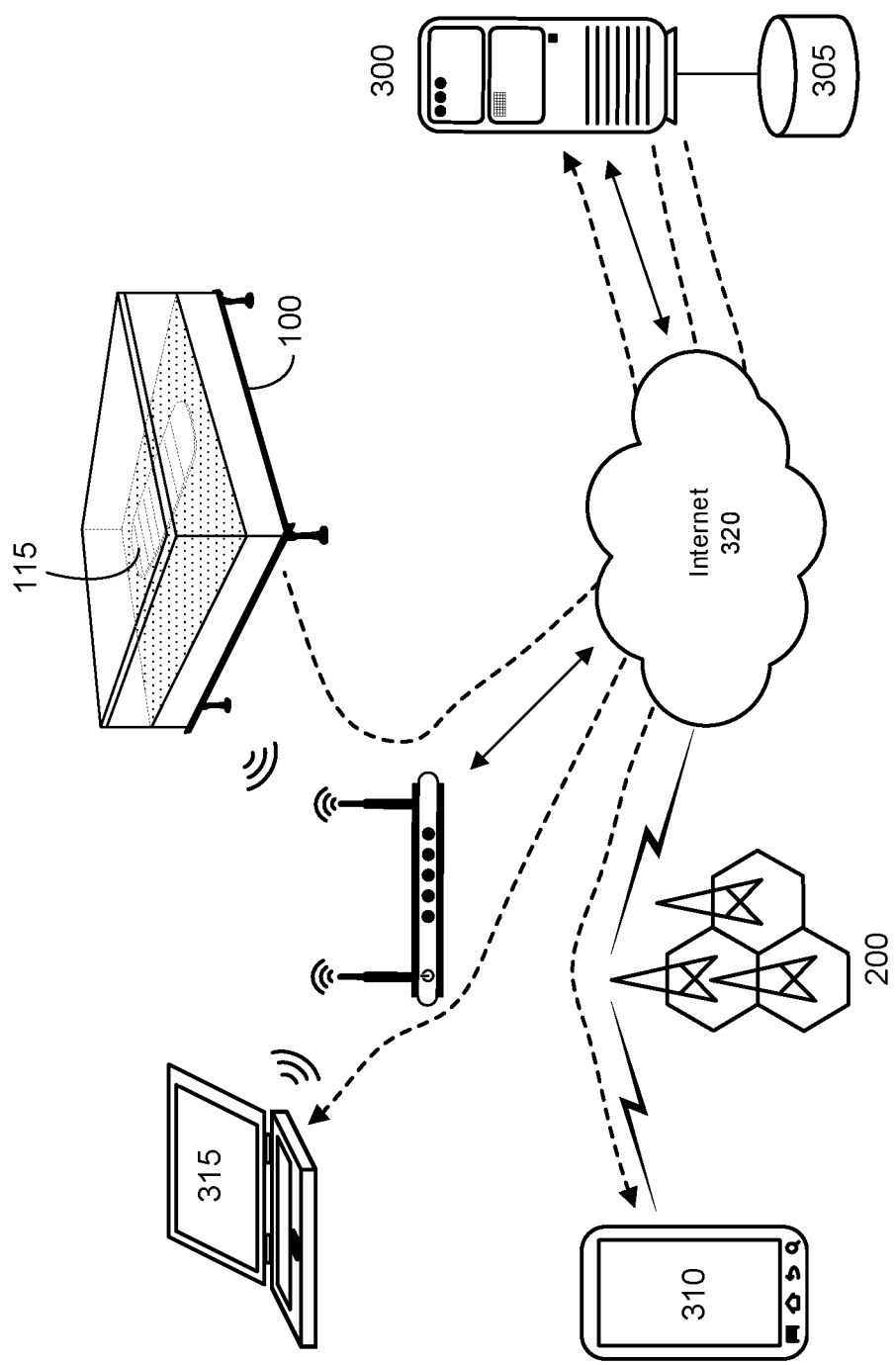
FIG. 3 depicts a communication architectures for obtaining data from a weight data sensor in accordance with one embodiment of the invention.

FIG. 3 depicts a communication architecture for obtaining data from a weight data sensor in accordance with one embodiment of the invention. In the embodiment of FIG. 3, weight data sensor (e.g., sensor 115 in bed frame 100 or sensor 25 in chair 200) wirelessly communicates over a LAN's Wi-Fi network through the Internet 320 to a hosted service 300 that stores weight data collected by weight data sensor 115 in database 305. Depending on embodiments, such communication may be direct or indirect, via a user's fitness device or health application on the individual's mobile device or smartphone. Hosted service 300 stores the weight data collected by the weight data sensor, performs analytics on the weight data and presents such weight data and analytics to the individual through a user interface, for example, through a web application accessible on a web browser (e.g., on laptop 310 or mobile device 315) or through an application installed on laptop 305 or mobile device 310. In an alternative embodiment, the weight data sensor may wirelessly communicate over a Bluetooth connection established with a user's laptop or mobile device (e.g., smartphone, tablet, etc.), which in turn, transmits weight data collected by the weight data sensor to hosted service 300 (e.g., through the LAN's Wi-Fi network and through the Internet). In certain embodiments, hosted service 300 may also receive other health-related data from other devices. For example, fitness bands or similar devices worn on the body of the individual may transmit heart rate, body temperature, ambient temperature, calories burned, steps walked, sleep patterns, location-based data and other data to hosted service 300 which can than combine such data with weight data collected from weight data sensor 115 and perform analytics thereon including as further discussed below. Such other health-related data is also stored in database 305, in addition to the weight data stored in database 305.

Figure 4:
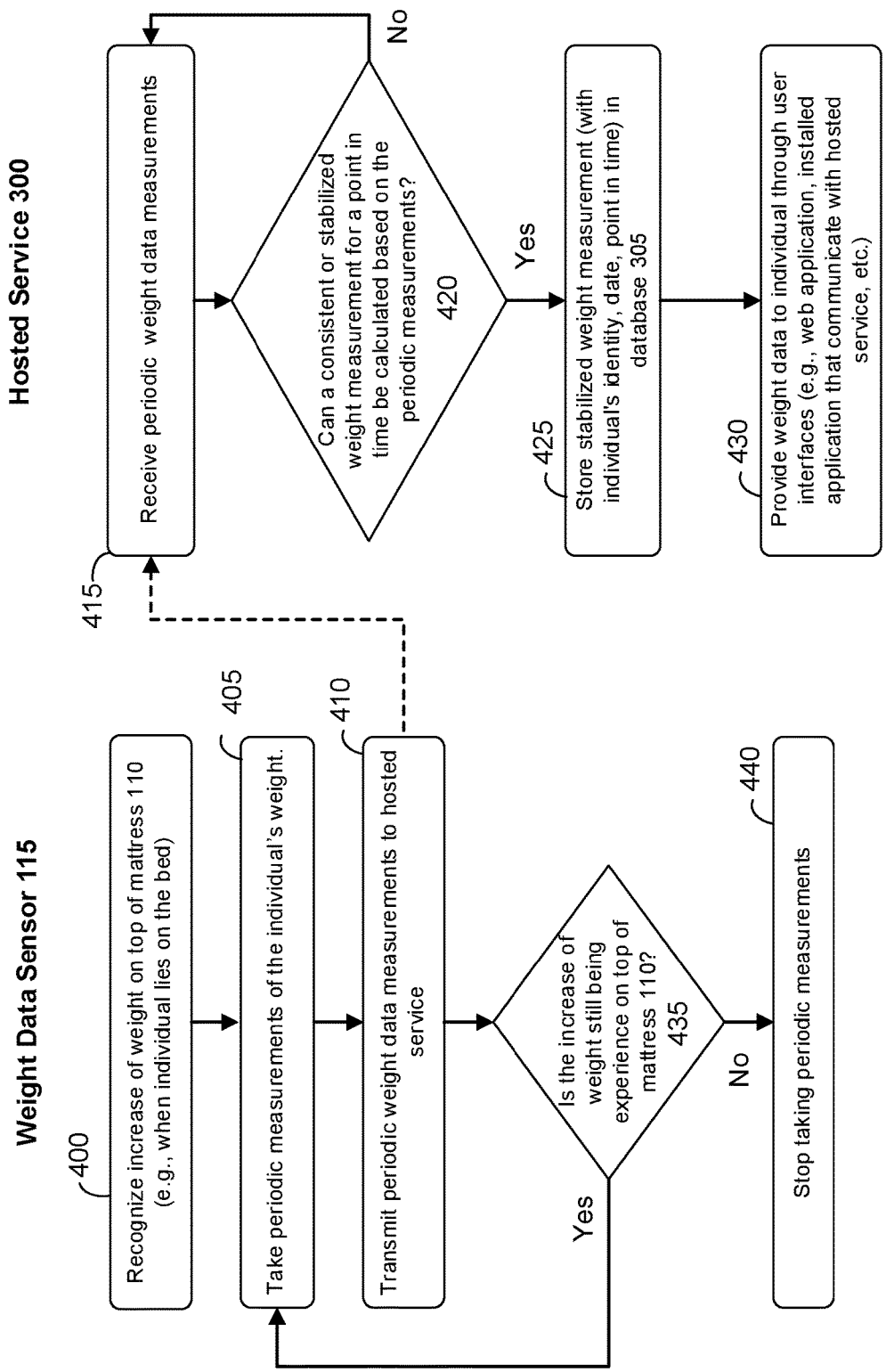
FIG. 4 depicts a flow chart for obtaining data from a weight data sensor in accordance with one embodiment of the invention.

FIG. 4 depicts a flow chart for obtaining data from a weight data sensor in accordance with one embodiment of the invention. In step 400, the weight data sensor recognizes an increase of weight on top of a furnishing, such as mattress 110 or chair 200, due, for example, to an individual going to bed for the evening or sitting down to work. In step 405, the weight data sensor may take a measurement or begin to take periodic measurements (e.g., every 30 seconds, every minute, every 5 minutes, every 30 minutes, or any similar period depending on embodiment) of the weight of the individual in order to calculate an accurate measurement of the individual's weight based on multiple measurements. If the furnishing is a bed, for example the individual may need to fall asleep or otherwise stop moving on mattress 110 before the weight data sensor can determine or otherwise calculate a consistent and/or stabilized weight of the individual. If the furnishing is a chair, the weight data sensor may be able to take an accurate measurement more quickly. In step 410, the weight data sensor transmits the individual's weight measurements to hosted service 300, which receives them in step 415.

Alternative embodiments may have the weight data sensor transmit its weight data to the individual's fitness band or smartphone, which in turn may either transmit the weight data to hosted service 300 or communicate amongst each other in order to ultimately communicate the weight data to hosted service 300. Furthermore, in certain embodiments, prior to step 410, the weight data sensor may confirm that either a fitness device of the individual or a smartphone of the individual (or a health application installed on the smartphone) is proximately located near the weigh data sensor (for example, through the confirmation of a Bluetooth connection between the weight data sensor and the fitness device and/or smartphone). Such a confirmation helps to increase the probability that the weight measurements related to the individual lying or siting on the bed or chair, rather than a different individual who is not in possession of the individual's fitness device or smartphone. In some embodiments if the fitness device or the smartphone are not confirmed to be proximate, the weight measurement is disregarded.

In the embodiment of FIG. 4, the transmitted weight measurements are the raw periodic measurements taken by weight data sensor 115. In step 420, hosted service 300 then performs heuristics and/or calculations to smooth the raw periodic measurements and determine whether a consistent and/or stabilized weight of the individual can be determined for a particular time based on the raw measurements. If, in step 420, a stable weight can be determined, then in step 425, hosted service 300 stores the stable weight measurement in database 305 in association with the individual's identity and the date (and possibly the particular time) and in step 430, provides such weight information to the individual through the user interface (e.g., web application, installed application on individual's device) as previously discussed. In certain embodiments, hosted service 300 is able to determine, based on comparisons with historic data (e.g., both weight data or other health-related data) stored in database 305, whether the determined weight is related or unrelated to the individual if, for example, multiple persons may sleep on mattress 110. In one example, if historic weight measurements are significantly different from the determined weight, hosted service 300 determines that the weight is unrelated to the individual. In certain embodiments, hosted service 300 may also receive other health-related data from other devices worn on the individual at generally the same time that weight measurements are received in step 415. If the received health-related data, such as a heart rate measurement from a fitness device worn by the individual, is significantly different than the historic measurements of the individual's heart rate while the individual is sleeping (as stored in database 305), then hosted service 300 could determine that the received weight measurement from the weight data sensor is unrelated to the individual (e.g., the individual is not sleeping in the bed, but rather actively awake elsewhere). And as previously discussed, in other embodiments, the weight data sensor may recognize when a fitness device that is worn by the individual is in close proximity to weight data sensor 115 (e.g., using proximity technologies such as Bluetooth or other similar radio communication technologies) and report such recognition to hosted service 300. If the fitness device is actively reporting other health-related data of the individual to hosted service 300 but is not in proximity to weight data sensor 115 when the determined weight is received in step 115, hosted service 300 may conclude that the determined weight is unrelated to the individual. In alternative embodiments, if the fitness device is not taking active measurements from the individual and is not in proximity to weight data sensor 115, weight data sensor 115 does not send any weight measurements to hosted service 305 in step 410. In yet other embodiments, weight data sensor 115 may recognize whether the individual's mobile device (such as a smart phone) is proximate to it before transmitting weight measurements to hosted service 300.

Similarly, hosted service 300 may, in step 425, disregard raw data measurements that cannot be smoothed to generate a stable weight or are otherwise inconsistent with past measurements for the individual (e.g., a pet has jumped onto the bed, a guest is sleeping on the bed, etc.) In the embodiment of FIG. 4, in step 435, if weight data sensor 115 continues to experience the increased weight of the individual (e.g., while the individual is sleeping throughout the night), the flow will return to step 405 and continue to take measurements until the increased weight has been removed (or otherwise stop taking the measurements in step 440). It should be recognized that alternative flows for obtaining data from a weight data sensor in accordance with embodiments different from FIG. 4. For example, rather than having hosted service 300 perform the calculations on the raw periodic weight data measurement in step 420, in alternative embodiments, weight data sensor 115 may itself perform such calculations (and related smoothing techniques) and determine a stable weight for a particular point in time prior to transmitting the stable weight data to hosted service 100. Similarly, in alternative embodiments, weight data sensor 115 may transmit the weight data (either raw or stabilized) to a corresponding application running on a local device, such as laptop 310 or mobile device 315 (e.g., via Bluetooth, etc.) which in turn transmits the received data to hosted service 300.

Figure 5:
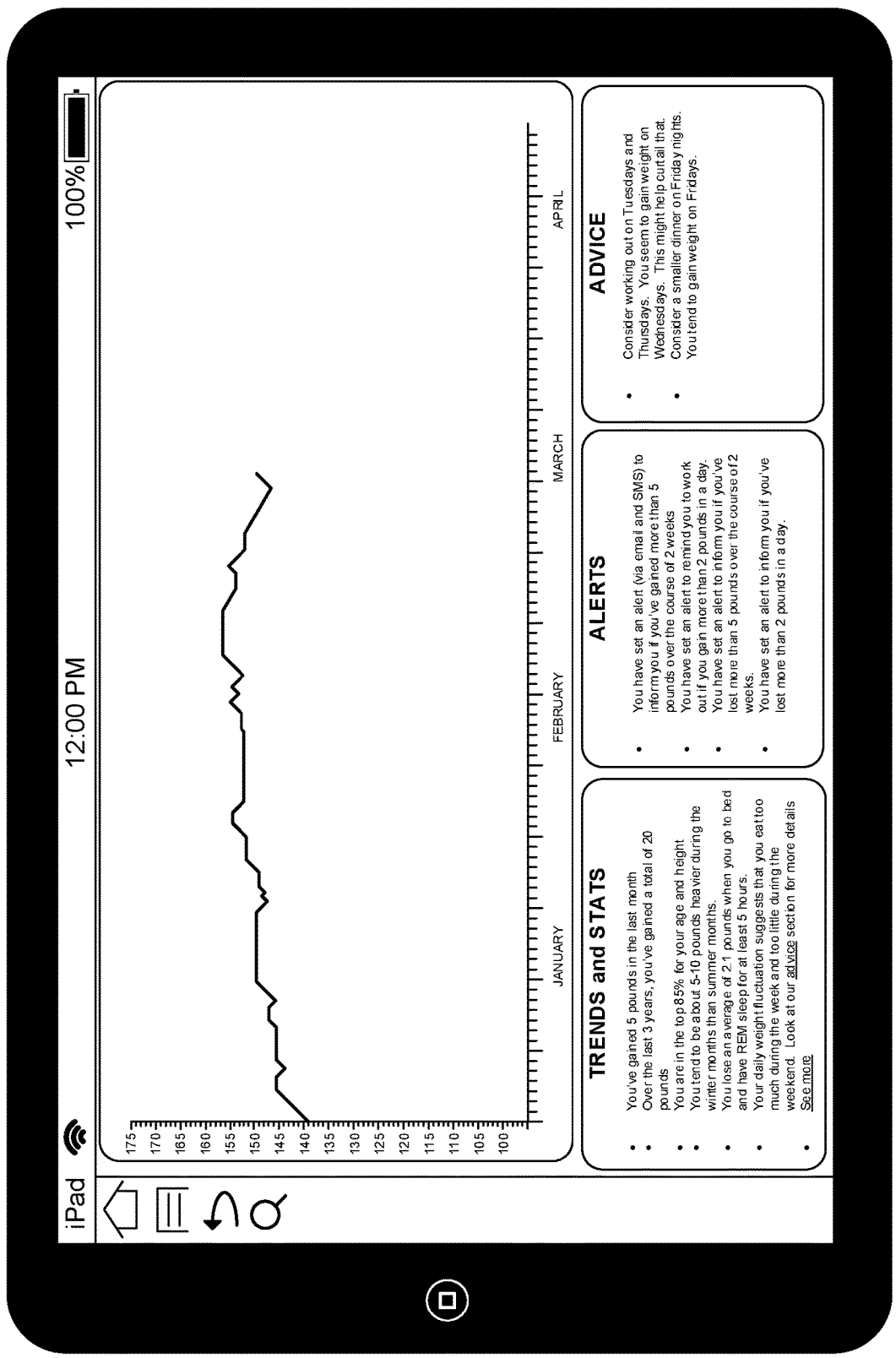
FIG. 5 depicts a user interface for an application that receives weight data in accordance with one embodiment of the invention.

FIG. 5 depicts a user interface for an application that receives weight data in accordance with one embodiment of the invention. The user interface of FIG. 5 may be displayed in an application installed on a computing device such as a tablet, smartphone, laptop, desktop or other computer system that communicates with hosted service 300 or may be displayed in a web application running on hosted service 300 that is accessible through a web browser running on any of the foregoing. Hosted service 300 performs all the analytics and other computing needed to provide the information that the user interface of FIG. 5 displays to the individual. As depicted in FIG. 5, user interface 500 depicts a historic trends and statistics of weight measurements for an individual. While the granularity of the weight measurements is shown as a daily measurement, embodiments of user interface 500 may enable an individual to change the granularity (e.g., weekly, monthly, etc.), for example, to view trends at different granularities. User interface 500 also enables the individual to set alerts to notify the individual (e.g., via text message, email, etc.) if certain criteria related to weight data are recognized. For example, the individual may wish to be alerted if he gains more than 5 pounds over the course of a few weeks. User interface 500 may also identify trends regarding an individual's weight data. For example, user interface 500 has identified a trend that the individual tends to gain weight during the weekdays and also tends to be 5-10 pounds heavier during the winter months. User interface 500 may also provide comparisons of an individual's weight data against similarly situated individuals. For example, user interface 500 has identified that the individual is in the top 85% in weight for persons with similar height and age. In embodiments in which weight data sensor 115 also measures sleep patterns such as REM sleep patterns (or where host server 300 is able to combine such sleep pattern-related data from other devices such as fitness bands that transmit data to host server 300 as previously discussed), user interface 500 may also combine actual weight data with such other data to provide trends and/or statistics relating to a combination of the data. For example, as depicted in FIG. 5, hosted service 300 recognizes that the individual loses an average of 2.1 pounds when the individual has at least 5 hours of REM sleep in a night. The embodiment of FIG. 5 also provides advice to the individual regarding his weight depending upon the weight data trends and the statistics, for example, encouraging the individual to exercise on certain days or eat light meals on certain days given weight gain patterns. It should be recognized that the user interface of FIG. 5 is merely exemplary and many other user interfaces may be developed consistent with the teachings herein.

The various embodiments described herein may be practiced with other computer system configurations including hand-held devices, microprocessor systems, microprocessor-based or programmable consumer electronics, minicomputers, mainframe computers, and the like. One or more embodiments of the present invention may be implemented as one or more computer programs or as one or more computer program modules embodied in one or more computer readable media. The term computer readable medium refers to any data storage device that can store data which can thereafter be input to a computer system computer readable media may be based on any existing or subsequently developed technology for embodying computer programs in a manner that enables them to be read by a computer. Examples of a computer readable medium include a hard drive, network attached storage (NAS), read-only memory, random-access memory (e.g., a flash memory device), a CD (Compact Discs) CD-ROM, a CD-R, or a CD-RW, a DVD (Digital Versatile Disc), a magnetic tape, and other optical and non-optical data storage devices. The computer readable medium can also be distributed over a network coupled computer system so that the computer readable code is stored and executed in a distributed fashion.

Although one or more embodiments of the present invention have been described in some detail for clarity of understanding, it will be apparent that certain changes and modifications may be made within the scope of the claims. Accordingly, the described embodiments are to be considered as illustrative and not restrictive, and the scope of the claims is not to be limited to details given herein, but may be modified within the scope and equivalents of the claims. In the claims, elements and/or steps do not imply any particular order of operation, unless explicitly stated in the claims.

Plural instances may be provided for components, operations or structures described herein as a single instance. Finally, boundaries between various components, operations and data stores are only exemplary, and particular operations are illustrated in the context of specific illustrative configurations. For example, while step 410 notes that the weight data sensor transmits the individual's weight measurements to hosted service 300, alternative embodiments may have the weight data sensor sending the weight data to a fitness device or a smartphone and having the fitness device and/or smartphone further analyze the data and/or send the weight data to hosted service 300. Other allocations of functionality are envisioned and may fall within the scope of the invention(s). In general, structures and functionality presented as separate components in exemplary configurations may be implemented as a combined structure or component. Similarly, structures and functionality presented as a single component may be implemented as separate components. These and other variations, modifications, additions, and improvements may fall within the scope of the appended claims(s).

I claim:

1. A method for tracking the weight of an individual who may be situated on a furnishing, the method comprising the steps of:
    receiving weight data at a weight data sensor that is situated to recognize a change in weight on the furnishing;
    confirming that a fitness device of the individual is proximately located to the weight data sensor;
    transmitting the received weight data to a hosted service, wherein the service provides a user interface to track weight patterns of the individual based on the received weight data;
    upon confirmation that the fitness device is proximately located to the weight data sensor, transmitting other health-related data from the fitness device to the hosted service;
    using the received other health-related data to determine whether the received weight data is unrelated to the weight of the individual; and
    disregarding the received weight data if the received weight data is determined to be unrelated to the weight of the individual.

2. The method of claim 1 wherein the furnishing is a chair or a bed.

3. The method of claim 1, wherein the other health-related data comprises at least one of heart rate, body temperature, body temperature, ambient temperature, calories burned, steps walked, sleep patterns and location based data.

4. The method of claim 1, further comprising, upon confirmation that the fitness device is proximately located to the weight data sensor, transmitting the weight data to the fitness device, wherein the fitness device performs the step of transmitting the received weight data to the hosted service.

5. The method of claim 1, further comprising, upon confirmation that the fitness device is proximately located to the weight data sensor, transmitting the weight data to a smartphone, wherein the smartphone performs the step of transmitting the received weight data to the hosted service.

6. The method of claim 5, wherein the received weight data and the received other health-related data are transmitted to the smartphone and received by the hosted service from the smartphone.

7. The method of claim 1, further comprising the step of notifying the individual of changes regarding the individual's weight.

8. A system for tracking the weight of an individual who may be situated on a furnishing, comprising:
    a weight data sensor for receiving weight data, wherein a form of the weight data sensor is designed to be situated to recognize change in weight on the furnishing and the weight data sensor is configured to measure and transmit weight data when the weight on furnishing differs from a default weight of the furnishing;

a fitness device of the individual for receiving other health-related data of the individual; and a remote server configured to (i) receive weight data from the weight sensor, (ii) receive other health-related data of the individual from the fitness device, (iii) determine whether the received weight data is unrelated to the weight of the individual by comparing the received other health-related data to past measurements of the other health-related data that correspond to past weight measurements of the individual, (iv) disregard the received weight data if the received weight data is determined to be unrelated to the weight of the individual, and (v) present a user interface to the individual to track weight patterns of the individual based on the received weight data.

9. The system of claim 8 wherein the furnishing is a chair or a bed.

10. The system of claim 8, wherein the other health-related data comprises at least one of heart rate, body temperature, body temperature, ambient temperature, calories burned, steps walked, sleep patterns and location based data.

11. The system of claim 8, wherein the user interface is a web application provided by a hosted service that is accessible by a web browser.

12. The system of claim 8, further comprising an application installed on a smartphone of the individual to present the user interface.

13. The system of claim 12, wherein the received weight data and the received other health-related data are transmitted to the smartphone and received by the hosted service from the smartphone.

14. The system of claim 8, wherein the remote server is further configured to notify the individual of changes regarding the individual's weight.

15. A method for tracking the weight of an individual who may be situated on a furnishing comprising the steps of:

receiving weight data from a weight data sensor that is situated to recognize a change in weight on the furnishing;

determining, by the weight data sensor, whether a smartphone of the individual is proximate to the weight data sensor;

disregarding the received weight data if the smartphone is not proximate to the weight data sensor; and if the smartphone is proximate to the weight data sensor, confirming that the received weight data is related to the individual based on other health-related data accessible by the smartphone and transmitting the received weight data to a hosted service configured provide a user interface to track weight patterns of the individual based on the received weight data.

16. The method of claim 15, wherein the furnishing is a chair or a bed.

17. The method of claim 15, wherein the step of transmitting the received weight data further comprises transmitting the received weight data to the smartphone of the individual.

18. The method of claim 15, further comprising disregarding the received weight data at the hosted service if the received weight data is inconsistent with historic weight and other health-related data stored at the hosted service and relating to the individual.

19. The method of claim 15, wherein the determining step comprises that a Bluetooth connection exists between the smartphone and the weight data sensor.

* * * * *